United States Patent [19]

Pedersen et al.

[11] Patent Number: 4,540,714

[45] Date of Patent: Sep. 10, 1985

[54] PROCESS AND CATALYST FOR THE PREPARATION OF A GAS MIXTURE HAVING A HIGH CONTENT OF METHANE

[75] Inventors: Karsten Pedersen, Birkerod; Jens R. Rostrup-Nielsen, Virum; Ib Greve H. Jorgensen, Bloustrod, all of Denmark; Kjeld J. Andersen, Umkirsch, Fed. Rep. of Germany

[73] Assignee: Haldor Torsoe A/S, Lyngbry, Denmark

[21] Appl. No.: 438,527

[22] Filed: Nov. 1, 1982

[30] Foreign Application Priority Data

Dec. 18, 1979 [DK] Denmark ............................ 5396/79

[51] Int. Cl.$^3$ .............................................. C07C 1/04
[52] U.S. Cl. .................................... 518/714; 518/721; 518/728
[58] Field of Search ..................... 518/714, 721, 728

[56] References Cited

U.S. PATENT DOCUMENTS 3,730,694  5/1973  Wunderlich.
4,151,191  4/1979  Happel et al..
4,177,202  12/1979  Chang et al..
4,260,553  4/1981  Happel et al. ........................ 518/714

FOREIGN PATENT DOCUMENTS 379335  8/1932  United Kingdom ................ 518/215

*Primary Examiner*—Howard T. Mars
*Attorney, Agent, or Firm*—Dennis P. Clarke

[57] ABSTRACT

A gas rich in methane is prepared by the methanantion of a synthesis gas containing carbon oxides, hydrogen and optionally other gases in the presence of one or more gaseous sulphur compounds, normally in an amount of at least 10 ppm preferably at least 200 ppm by volume, calculated as $H_2S$, with the aid of a catalyst comprising vanadium and/or molybdenum, which during the process is present as one or more sulphides, on a support comprising titanium dioxide.

A high activity and a high selectivity for methane are obtained. A further advantage is that, by far, the main constituent of the higher hydrocarbons formed is ethane, which, by conversion into ethylene, is an important raw material in petrochemical synthesis.

The selectivity for methane formation may be further improved by promoting the catalyst with compounds, especially sulphides of metals of groups IA, IIA and/or IIIB, particularly cerium.

The invention also relates to the catalyst itself which may be prepared by impregnation or coprecipitation techniques.

4 Claims, No Drawings

PROCESS AND CATALYST FOR THE PREPARATION OF A GAS MIXTURE HAVING A HIGH CONTENT OF METHANE

FIELD OF THE INVENTION

The present invention relates to a process for the preparation of a gas mixture having a high content of methane by the catalytic conversion of a synthesis gas containing hydrogen and carbon oxides and optionally other gases.

BACKGROUND OF THE INVENTION

Synthesis gas is prepared predominantly by gasification, i.e., by steam treatment of coal or heavy petroleum fractions, in the first-mentioned case by the reaction:

$$C + H_2O \rightarrow CO + H_2 \qquad (1)$$

accompanied, however, by side reactions such that carbon dioxide and a little methane are also formed. By the gasification of petroleum fractions the amount of hydrogen produced in the synthesis gas is higher. Some coal and petroleum gasification processes involve the formation of greater amounts of methane, other hydrocarbons, tar, etc. During gasification a small amount of oxygen is normally added in order to render the gasification self-supplying with heat.

By various reactions the synthesis gas may be converted predominantly into methane and in recent years such reactions have gained an ever-increasing importance, i.e., for preparing substitute natural gas (SNG), component of special gas transport systems and to increase the energy supply. These reactions include:

$$CO + 3H_2 \rightleftharpoons CH_4 + H_2O \qquad (2)$$

$$2CO + 2H_2 \rightleftharpoons CH_4 + CO_2. \qquad (3)$$

The carbon dioxide may, however, also be converted with hydrogen into methane:

$$CO_2 + 4H_2 \rightleftharpoons CH_4 + 2H_2O. \qquad (4)$$

The so-called "shift reaction" causes an equilibrium between carbon monoxide and carbon dioxide:

$$CO + H_2O \rightleftharpoons CO_2 + H_2. \qquad (5)$$

Methane may also be formed as a by-product in the Fischer-Tropsch synthesis (hereinafter referred to as the FT-synthesis):

$$2nCO + (n+1)H_2 \rightarrow C_nH_{2n+2} + nCO_2 \qquad (6)$$

(paraffin reaction)

$$2nCO + nH_2 \rightarrow C_nH_{2n} + nCO_2 \qquad (7)$$

(olefin reaction), and possibly also:

$$nCO + 2nH_2 \rightarrow C_nH_{2n} + nH_2O \qquad (8)$$

(olefin reaction).

The FT-synthesis predominantly produces higher hydrocarbons and is especially employed for the preparation of motor fuel and other liquid fuels. By a suitable choice of catalyst and process conditions it may yield a rather high proportion of methane.

A good review of methanation processes and catalysts is given by Mills et al in Catalysis Review 8(2), pp. 159–210 (1973).

The best catalyst for the preparation of methane from carbon oxides and hydrogen according to reactions (2), (3), and (4) is nickel on a support which normally consists of one or more refractory oxides e.g., chromium oxide, γ-alumina, magnesium oxide, or silica, or mixtures thereof. Nickel may be present as oxide but during the methanation process in the strongly reducing environment it is predominantly present as free metal. Nickel is still the most important catalyst for methane production but nickel catalysts have the drawback that they are exceedingly sensitive to sulphur poisoning. The feed gas for a nickel catalyzed methanation process must, to a very high degree, be freed from sulphur, specifically from gaseous sulphur compounds. In practice the sulphur content is kept below 0.1–0.01 ppm by vol., dependent on the content of $H_2$ in the synthesis gas and the temperature at the inlet to the catalyst bed. The sulphur deposition on the catalyst decreases with decreasing value of the ratio $H_2S/H_2$ and increasing temperature (see J. R. Rostrup-Nielsen, "Steam Reforming Catalysts", Teknisk Forlag, Copenhagen 1975). The specificity for methanetion formation also decreases strongly with increased sulphur poisoning (see J. R. Rostrup-Nielsen and Karsten Pedersen, J. Catal. 59, p. 395 1979) for which reason it is normally desired that the sulphur coverage should be below 10%. Since the feed materials from which the feed gas is prepared, i.e., gasified coal or heavy fuel oil, as a rule are strongly sulphur-containing the feed gas for the methanation reaction must be subjected to an expensive and time-consuming sulphur purification process. The majority of metals have been used as Fischer-Tropsch catalysts, either as such or as oxides or hydroxides or possibly in a surface-sulphided form, but all the known catalysts are sulphur sensitive to a higher or lesser degree. This especially holds true for the important methanation and FT catalysts which are based on iron, cobalt or ruthenium.

Karla Wencke showed (Freiburger Forschungsh, A151, pp. 11–29 (1960)) that molybdenum as the free metal or oxide catalyzed the methanation of a synthesis gas with CO and $H_2$, that it was advantageous to operate in a fluid bed and that the activity of the Mo-based catalysts for methane production decreased when small amounts of sulphur compounds were present in the synthesis gas. Madon and Shaw state in a reviewing paper in Catal. Review-Sci. Eng. 15(1), pp. 69–106 (1977)) that FT-catalysts based on metallic, oxidic or surface-sulphided molybdenum are subject to reduced activity in the presence of $H_2S$ in the synthesis gas but that the effect is temporary and reversible so that the initial activity of the catalyst returns when sulphur is removed from the feed gas stream. In this respect molybdenum is different from, for example, nickel and ruthenium based catalysts in which the poisoning can be considered definitive and lasting because of strong affinity of these catalysts for sulphur and because the chemisorbed sulphur is in equilibrium with very low concentrations of $H_2S$. Madon and Shaw also call attention to the fact that a catalyst based on molybdenum sulphide is strongly selective for methane formation (more than 90% of the carbon present in the feed converted into hydrocarbons is converted into methane) but that the presence of larger amounts of H₂S in the feed gas causes a shift so that almost 30% are converted into C₃₋₄-hydrocarbons and only about 60% into methane.

From South African patent specification No. 766,137 it is known that, i.e., thoria, zirconia, hafnia and titania are FT-catalysts and comparatively sulphur-resistant. However, their catalytic activity is low and moreover they are selective to a considerable degree for forming aromatic and other higher hydrocarbons. The specification first and foremost is concerned with the use of vanadium based catalysts for making methane and test results with various forms of vanadium are set forth. It was found that a pre-sulphided catalyst of $V_2O_5$ on a zeolite support has higher activity and selectivity for the formation of methane in the presence of up to 2% by volume of $H_2S$ in the feed gas than without. Similar results were obtained with pure vanadium oxide (without support) and a similar yet improved activity was obtained with a high concentration of vanadium oxide on a support of alumina.

However, the activity and specificity of vanadium catalysts for methanation are not very high and in order to obtain a reasonably satisfactory activity a high concentration of vanadium on the catalyst is necessary, whether as oxide or sulphide. Correspondingly, known molybdenum catalysts are not satisfactory for methane production, partly because the activity is not satisfactory, partly because the activity usually decreases in the presence of sulphur, and particularly because known molybdenum catalysts favor higher hydrocarbons, notably $C_{3-4}$-hydrocarbons, at the expense of methane.

Vanadium and molybdenum based catalysts are known for various other purposes. Thus, U.S. Pat. No. 2,605,238 discloses a catalyst composition for use in vaporphase processes for the partial oxidation of organic compounds, e.g., for the manufacture of maleic anhydride from butylene. The catalyst consists essentially of a molybdenum trioxide and amorphous titanium dioxide. U.S. Pat. No. 3,464,930 discloses a catalyst for the gas phase oxidation of aromatic or unsaturated aliphatic hydrocarbons into carboxylic acid. The catalysts consist of an inert non-porous carrier coated with a mixture of vanadium pentoxide and titanium dioxide. U.S. Pat. No. 3,565,829 discloses a supported catalyst for oxidation reactions, e.g., the oxidation of o-xylene into phthalic anhydride. The catalyst comprises a non-porous support material and thereon a thin layer of an active composition consisting of a mixture of vanadium pentoxide, titanium dioxide and at least one oxide of aluminum, lithium and/or zirconium. German published patent application No. 24 36 009 discloses a supported catalyst for the oxidation of o-xylene or naphthalene into phthalic anhydride, comprising an inert, non-porous support with a thin coating of vanadium pentoxide, titanium dioxide and rubidium and/or cesium.

None of these methods and catalysts are usable for methane production and hence there still exists a need for providing a synthesis gas conversion which utilizes a catalyst which is fully sulphur-resistant, which is highly selective for producing methan and which has a high activity.

SUMMARY OF THE INVENTION

This object is achieved by the present invention which provides a catalyst and process for the preparation of a gas mixture having a high content of methane by the catalytic conversion at a pressure of 1–150 bar and a temperature of 250°–850° C. of a synthesis gas (feed gas) containing hydrogen and carbon oxides and optionally other gases, wherein the feed gas contains at least 10 ppm (calculated as $H_2S$) of one or more sulphur compounds. The conversion takes place in the presence of a catalyst containing vanadium and/or molybdenum in the form of free metal, salt, oxide, or sulphide, on a porous, oxidic support consisting essentially of titanium dioxide.

The method and catalyst of the invention enable the production from the above-described feed gas of a product gas consisting predominantly of methane, e.g., containing at least 50%, by weight, preferably 60 to about 99%, by weight, of methane, based upon the amount of carbon contained in the feed gas which is converted into hydrocarbons. The method and catalyst of the invention are also advantageous in that a high proportion of the higher hydrocarbons produced, i.e., $>C_1$, is in the form of $C_2$-hydrocarbons.

The invention also relates to a catalyst for use in the process. In accordance with the invention this catalyst comprises vanadium and/or molybdenum in the form of free metal, salt, oxide, or sulphide on a porous oxidic support consisting essentially of titanium dioxide. Advantageously the catalyst is promoted with one or more salts, hydroxides, oxides or sulphides of one or more metals belonging to groups I-A, II-A and/or III-B in the Periodic Table. Preferably the catalyst is vanadium sulphide promoted with cerium sulphide on a support substantially only consisting of porous titanium dioxide.

DETAILED DESCRIPTION OF SPECIFIC EMBODIMENTS

It has been found that the catalysts described above possess a high activity and high selectivity for methane formation. They not only catalyze reactions (2)–(4) and/or (6)–(8) but also the shift reaction (5). By the conversion a high proportion of methane results in the product gas and part of the carbon monoxide converted is converted into higher hydrocarbons. It is surprising and a special advantage of the present process that the proportion converted into higher hydrocarbons is preferentially converted into $C_2$-hydrocarbons (ethane and ethylene). The reason for this latter circumstance is as follows, although it is to be understood that we do not wish to be bond by the following explanation:

The Fischer-Tropsch synthesis is a type of polymerization reaction in which the yield structure follows the so-called Flory distribution (see, for instance, G. HenriciOlive et al, Angew. Chemie, 15, page 136, 1976, and H. Schultz et al, Fuel Proc. Technol. 1, page 31, 1977), a theoretical distribution of the various chain lengths which can be deduced mathematically on simplified kinetic assumptions. It can be shown that the Flory distribution theoretically can give a maximum yield of about 27% by weight of ethane and/or ethylene, calculated on the amount of carbon in the synthesis gas converted into hydrocarbons. In practice the yield of $C_2$-hydrocarbons in FT synthesis is almost always considerably below that theoretically expected according to the Flory distribution and only in a few cases has it been possible, under special circumstances, to obtain a $C_2$-hydrocarbon yield corresponding to or above that according to the Flory distribution. By using the above-mentioned catalysts the ethane and ethylene content can constitute almost the entire non-methane amount of hydrocarbons in the product gas and it can often be above the theoretical maximum amount of $C_2$ according to the Flory distribution.

As mentioned, the methane is primarily used as fuel, e.g., SNG, or as part of energy transport systems, and small amounts of higher hydrocarbons are permissible or even desirable since small amounts thereof are often present in natural gas. They act to increase the calorific value of the gas. Larger amounts of higher hydrocarbon, particularly $C_2$-hydrocarbons in the product gas as a rule are not desired. If such larger amounts are formed by the present process, however, they may be separated off and utilized as or converted into a valuable raw material for organic syntheses in the petrochemical industry. Ethylene is much used as such and ethane and $C_3$-hydrocarbons can easily be cracked to ethylene in high yield.

As a feed gas for the method of the present invention, there can be employed synthesis gas having varying contents of hydrogen and carbon oxides, mainly in the form of carbon monoxide, an optionally also containing other gases such as steam, methane and small amounts of other hydrocarbons. Amounts of nitrogen and the inert gases, for example from combustion air, will not affect the process. The volume ratio of hydrogen to carbon monoxide will typically be from about 0.4:1 to about 3:1, preferably close to equal parts of hydrogen and carbon monoxide as is obtained according to equation (1) above. It is a special advantage of the process that it can be carried out at such low amounts of hydrogen since there is saved the work and expense involved in enriching the synthesis gas with hydrogen. It known methanations it is usually necessary to maintain a higher volume ratio (mole ratio) $H_2/CO$ than 1 in order to avoid the formation of free carbon on the catalyst according to the exothermal Boudouard reaction $$2CO \rightarrow C + CO_2 \qquad (9)$$

The carbon formation causes irreversible damage to the catalyst and the reaction therefore imposes limitations of the usable process parameters. It has been found that the sulphur addition stated above suppresses the carbon formation and also the formation of graphite (so-called "gum-forming" reaction) which often procedes the carbon formation and consists of a polymerization to form long carbon chains having a low content of hydrogen (see Rostrup-Nielsen and Karsten Pedersen, loc. cit.).

It is important that sulphur be present in the synthesis gas (feed gas) in the form of one or more gaseous sulphur compounds because the sulphur establishes the catalytically active sulphide phase of the catalyst metal. The amount of sulphur is not overly critical since the amount of sulphur needed to preserve the active sulphide phases is very low compared to the amount of gas to be reacted. The minimum amount of sulphur is about 10 ppm, calculated as $H_2S$ on the volume of the feed gas. In most cases the practical minimum amount will be 200 ppm by volume and very frequently the content will be 1000 ppm by volume or more, e.g., 1000-3000 ppm by volume, still calculated as $H_2S$. Increased amounts of sulphur can be considered advantageous for the activity of the catalyst and there is no critical upper limit for the content of gaseous sulphur compounds. In practice, however, it will rarely be necessary to exceed about 2% by volume, calculated as hydrogen sulphide. This in practice means that it is not at all necessary to remove sulphur from the synthesis gas or from the raw materials such as coal or heavy oil gasified to synthesis gas. The amount of sulphur is not overly critical and neither is the type of the gaseous sulphur compound. As examples may be mentioned hydrogen sulphide, sulphur dioxide, carbonyl sulphide, carbon disulphide, mercaptans, thioethers, disulphides and thiophene.

The methanation of the synthesis gas may take place at low pressures, such as atmospheric pressure, but will in practice always be carried out at elevated pressure. The working pressure is not critical and will mainly be determined by practical considerations such as the pressure at which the gasification is carried out and hence the synthesis gas formed, which will frequently be on the order of magnitude of 5-150 bar, as well as the pressure at which it is desired to use the methane formed. Under otherwise equal conditions an increase in pressure promotes the formation of $C_2$-and higher hydrocarbons and a decrease in pressure promotes the formation of methane. It will normally be expedient to operate the reaction at a pressure of 15-150 bar, especially 20-100 bar, although both lower and higher pressure may, as stated above, be utilized.

The temperature employed is critical to the process. It cannot be carried out at a reasonable rate of reaction at temperatures below 250° C., and, in practice, considerably higher temperatures are preferred. Methane formation by reaction (2)-(4) as well as the formation of higher hydrocarbons by reactions (6)-(8) are exothermal and it will frequently cause greater difficulties to keep the temperature down rather than elevated. High temperatures favor the formation of methane whereas lower temperatures favor the formation of higher hydrocarbons. With regard partly to this, partly to the stability of the catalysts and reactors at higher temperatures, it is normally preferred according to the invention to carry out the methanation at a temperature of 250°-850° C., preferably 300°-700° C., for example, 350°-600° C.

The metal, vanadium and/or molybdenum, is present in the freshly prepared catalyst in the form of free metal, salt, oxide or sulphide. It is not overly important which of these forms is employed since it must be assumed that the salt and oxide are reduced to free metal under the presence of the hydrogen in the synthesis gas, and that the free metal is sulphided under the influence of the sulphur compound in the synthesis gas to some sulphidic compound, mono-, di- or polysulphide so that the catalyst during the process itself always is present as sulphide.

The amount of catalyst metal is not critical but usually is in the range 1-50% by weight, calculated as metal oxide on the weight of the entire catalyst, calculated as metal(s) or metal compound(s) and support. In practice the amount of catalyst metal most often will be on the order of magnitude 3-40%, preferably 5-30%, calculated in the same manner. If the catalyst is promoted as discussed hereinbelow, the amount of vanadium and/or molybdenum, calculated in the manner stated, is below the highest of the above values.

The vanadium and/or molybdenum compound and the optional promoter are deposited, preferably by impregnation, on a porous support consisting essentially of titanium dioxide. It has been found that titanium dioxide increases the activity of the catalyst significantly without substantially reducing its selectivity for methane formation.

It is known to promote FT and methanation catalysts with compounds of alkali or alkaline earth metals whereby graphite and carbon formation reactions are suppressed. It has been found that it may be particularly advantageous to promote the catalyst employed in the present process with one or more compounds, particularly salts, oxides, hydroxides or sulphides, of one or more metals of group IA (the alkali metals), IIA (the alkaline earth metals) or IIIB (Sc, Y, the actinides and the lanthanides). It has been found that such a promoter increases the selectivity for methane formation. If such a promoter is present, it should preferably constitute a lesser proportion of the entire catalyst weight than the vanadium or molybdenum component.

The catalyst is prepared by techniques known in the art. The support may for instance be formed by precipitation from a suitable solution of a salt or other compound of titanium, drying and optionally calcination, yet with care so that sintering is not caused to such a high degree that the pore volume and thereby the specific inner surface area becomes too small. Specific surface areas of the order of magnitude of 10 $m^2/g$ and above, especially of 20-300, for instance 100-200 $m^2g$, are desirable.

Before drying and calcination the support material is shaped into suitable bodies, for examples, pellets, tablets or rings. The bodies formed thereafter are impregnated with a solution, preferably aqueous solution of a suitable compound of vanadium and/or molybdenum, whereby the catalyst metal is deposited on the support. Drying and calcination are then carried out to convert the catalyst metal into oxide. The bodies thus formed are ready for use. Large bodies may, however, if desired prior to or after the impregnation, be crushed to smaller, irregular fragments.

The finished catalyst, in which the catalyst metal is present as oxide, may, if desired, be pre-sulphided to convert the oxides into sulphides (mono-, di-, poly-, and/or oxysulphides), however, this conversion may be omitted since it will automatically take place during hydrocarbon synthesis in the presence of gaseous sulphur compounds. The pre-sulphiding can, for instance, be carried out with hydrogen sulphide or carbon disulphide in hydrogen.

The catalyst may also be prepared by a coprecipitation technique in which metal salts of vanadium and/or molybdenum together with salts or oxides of titanium are precipitated as hydroxides by the addition of, for instance, alkali metal hydroxide or alkaline earth metal hydroxide or basic ammonium compounds. The precipitated material is filtered, washed and dried. A subsequent calcination sets the hydroxides into oxide form. The material is shaped into suitable bodies, e.g., granulate, tablets or rings. An after-calcination may optionally be carried out in order to increase the strength of the catalyst, which is thereupon optionally sulphided as described above.

According to the invention the catalyst particularly advantageously contains vanadium in the form of free metal, salt, oxide or preferably sulphide on a support substantially consisting of porous titanium dioxide. By "substantially" in this connection is meant that small amounts of impurities may be present, originating from the titanium raw material or the salts or other compounds from which the support material has been precipitated during the preparation.

Very advantageously according to the invention the catalyst consists of one or more sulphides of vanadium and one or more sulphides of cerium on a catalyst substantially consisting of porous titanium dioxide.

The methanation reaction is conducted substantially according to well-known Fisher-Tropsch and methanation reaction techniques. Thus, the catalyst is placed preferably as a fixed bed in a reactor into which the synthesis gas is passed via suitable lines, optionally in a preheated condition. The reaction is exothermal and it is therefore necessary to limit the temperature increase in the reactor, which can be accomplished in a variety of ways. The reactor may be an adiabatic reactor where part of the product gas is recycled and mixed with the feed gas, which is thereby diluted with an ensuing limitation of the temperature increase. Advantageously the reactor may be a cooled reactor wherein the catalyst is placed in tubes surrounded by a cooling medium such as boiling water, boiling Dowtherm ® (high-boiling heat transfer media) or flowing gas, or vice versa. Possibly an adiabatic and a cooled reactor may be combined according to principles similar to those described in U.S. patent application Ser. No. 99,361. Irrespectively of which of the principles mentioned is utilized, the reaction may be operated with or without recycling of part of the product gas whereby the temperature increase is reduced. It is also possible to conduct the reaction in a fluidized catalyst bed with cooling.

The main purpose of the product gas is utilization of the methane formed as a fuel, notably SNG. Small amounts of higher hydrocarbons, especially ethylene as well as ethane and propane, after steam cracking into ethylene, may be used as a petrochemical raw material. When the synthesis is carried out with a $H_2/CO$ ratio close to 1:1 a substantial part of the product gas, about half, will be present as $CO_2$. This carbon dioxide must be removed if the hydrocarbons are to be separated, and when the main part is to be used as fuel. The separation of carbon dioxide can be accomplished by well-known methods and does not form any part of the invention. Separated carbon dioxide may, if desired, be used as the oxidation agent in cases where the synthesis gas has been prepared from natural gas or liquid hydrocarbons.

If the $H_2/CO$ ratio in the synthesis gas is below 1, as is the case with some gases formed by the gasification of coal, the required amount of hydrogen for the methanation may be obtained by adding steam to the synthesis gas. Concurrently with the hydrocarbon/methane reaction the catalyst will then cause the necessary hydrogen to be formed via the shift reaction (5).

The process of the invention is illustrated by the following non-limiting example.

EXAMPLE 1

Catalysts according to the invention and comparison catalysts were prepared in the following manner:

Ceramic support of $TiO_2$ and, for comparison, of $Al_2O_3$ in the form of irregular small particles of the size (determined by sieve) 0.5-1 mm and a specific surface area of about 200 $m^2/g$ were impregnated with either ammonium vanadate or ammonium molybdate in ammonical solution while adding about 2% by volume of alkanol amine to avoid precipitation of metal hydroxides. After air drying overnight there was calcined by heating in air at 550° C. for four hours whereby salt residues were removed. Hereafter the metals were present on the catalyst as oxides. The catalysts were activated by sulphiding by heating under nitrogen at atmospheric pressure at 300° C. and replacing of the nitrogen stream with a stream of 2% by volume of hydrogen sulphide in hydrogen. The content of V or Mo on the unused catalysts is seen in Table I hereinafter, the support constituting the entire weight beyond catalyst metal and sulphur. The testing of the catalysts was carried out with a synthesis gas consisting of 48% by volume $H_2$, 48% CO, 1% $H_2S$ and 3% Ar, the last-mentioned of which serves as an internal standard, e.g., for determining the gas concentration during synthesis. The pressure of the synthesis gas stream was +bar and space velocities of 2000–3000 Nl/h/kg were used.

Two series of experiments were carried out under the conditions described. The first series was carried out at a temperature of 300° C. and served at determining the standard activities. The second series of experiments was carried out at 450° C. and served at determining the distribution of hydrocarbons.

The results appear from the Table below. The standard activity is the amount of carbon monoxide that has reacted to form hydrocarbons, expressed as Nl $C_1$/kg catalyst/hour, the amount of higher hydrocarbons having been calculated as the equivalent amount of methane and added to the amount of methane. The standard activity has, moreover, been calculated on the basis of the content of catalyst metal so that catalyst having different metal content can be compared directly. The Table also shows the distribution of the hydrocarbons formed in the synthesis, whereby $C_1$-means methane, $C_2$-ethane, and $C_3$-propane. The amount of the individual hydrocarbons has been stated in % by weight, calculated on the distribution of the carbon therein; accordingly, the figures show the amount of carbon converted into the hydrocarbon in question, expressed as proportion of the carbon of CO of the feed gas converted into hydrocarbons. In the experiments also other hydrocarbons were formed, especially ethylene, but in very small amounts.

In the Table experiments Nos. 1, 3 and 4 are in accordance with the invention; Nos. 2 and 5 are comparison experiments with a support of alumina. The Table shows that replacement of the alumina support with a titanium dioxide support roughly speaking does not influence the selectivity for methane formation but increases the activity, relative to the amount of V or Mo. For a catalyst containing vanadium the activity was increased 3,5 times and with molybdenum the increase was 5 times. The Table also shows that almost the entire amount of hydrocarbons beyond methane occurs as ethane, especially when using the vanadium catalysts, and that the hydrocarbon distribution thus is radically different from the Flory distribution and especially from the distribution normally obtainable in FT synthesis.

In the experiments small amounts of C were formed on the catalysts but the amount was so small (about 0.2%) that it did not have any significance.

During the synthesis first and foremost reactions (2), (3), (4), and (5) takes place and furthermore (6) and (7), which are supposed to be irreversible at temperatures below 500° C. and to take place via $CS_2$ and/or COS. Reaction (5) is reversible and faster than the hydrocarbon reactions.

TABLE

| Catalyst No. | % V or Mo | Support | Standard Activity $NlC_1$/h/kg cat | Standard Activity $NlC_1$/h/kg metal | Distribution of carbon converted into hydrocarbons, by weight(++) $C_1-$ | $C_2-$ | $C_3-$ |
|---|---|---|---|---|---|---|---|
| 1 | 6,2 V | $TiO_2$ | 183 | 2950 | 94 | 6 | <1 |
| 2 | 6,7 V | $Al_2O_3$ | 58 | 850 | 96 | 4 | <1 |
| 3 | 7,9 Mo | $TiO_2$ | 320 | 4100 | 88 | 11 | 1 |
| 4 | 6,3 Mo | $TiO_2/Al_2O_3$(+) | 182 | 2890 | 90 | 10 | <1 |
| 5 | 12,5 Mo | $Al_2O_3$ | 149 | 815 | 93 | 7 | <1 |

(+)The ratio $TiO_2$ to $Al_2O_3$ in this support is 1:1 by weight
(++)Rounded to whole numbers.

The method and catalyst of the present invention enable the conversion of a feed gas having a composition as described hereinabove to a product gas wherein the predominant hydrocarbon produced is methane. By "predominant hydrocarbon" is meant that at least 50%, preferably 60 to about 99%, by weight of the product gas, based on the amount of carbon in the feed gas converted to hydrocarbons is methane.

Moreover, as is apparent from the results set forth in the table above, the catalysts of the present invention supported on titania is more specific to the production of methane and has a higher degree of activity than the same catalysts supported on alumina.

We claim:

1. In a process for the conversion of a synthesis gas mixture containing hydrogen, carbon oxides and at least one other gas to a methane-containing gas mixture by catalytic conversion, the improvement wherein said synthesis gas mixture contains at least one gaseous sulfur compound in an amount of at least 10 ppm, calculated as $H_2S$, and said conversion is conducted at a temperature of 250°–850° C. and a pressure of 1–150 bar in the presence of a catalyst consisting of at least one component selected from the group consisting of vanadium and molybdenum, salts, oxides and sulfides thereof, said catalyst being deposited on a support consisting of porous titanium dioxide, whereby the product gas mixture contains at least 50%, by weight, of methane based on the amount of carbon in said synthesis gas mixture converted to hydrocarbons.

2. The process of claim 1 wherein said catalyst consists of vanadium sulfide.

3. The process of claim 1 wherein said catalyst consists of molybdenum sulfide.

4. The process of claim 1 wherein said conversion is carried out at a temperature of 30°–700° C. and a pressure of 2–100 bar.

* * * * *

UNITED STATES PATENT AND TRADEMARK OFFICE
CERTIFICATE OF CORRECTION

PATENT NO. : 4,540,714

DATED : September 10, 1985

INVENTOR(S) : PEDERSEN et al

It is certified that error appears in the above-identified patent and that said Letters Patent is hereby corrected as shown below:

Cover page, Assignee: change "Torsoe" to --Topsoe--;
Cover page, below "Filed: November 1, 1982" insert
      --Related U.S. Application Data
  Continuation-in-part of Ser. No. 215,547, Dec. 11, 1980, abandoned.--;
Column 2, line 27, change "methanetion" to --methane--;
Column 3, line 61, change "methan" to --methane--;
Column 5, line 19, change "an" to --and--;
Column 5, line 31, change "It" to --In--;
Column 9, line 7, after "was", delete "+" and insert --30--.

Signed and Sealed this

Twenty-first Day of January 1986

[SEAL]

Attest:

DONALD J. QUIGG

Attesting Officer

Commissioner of Patents and Trademarks